Figure 1:
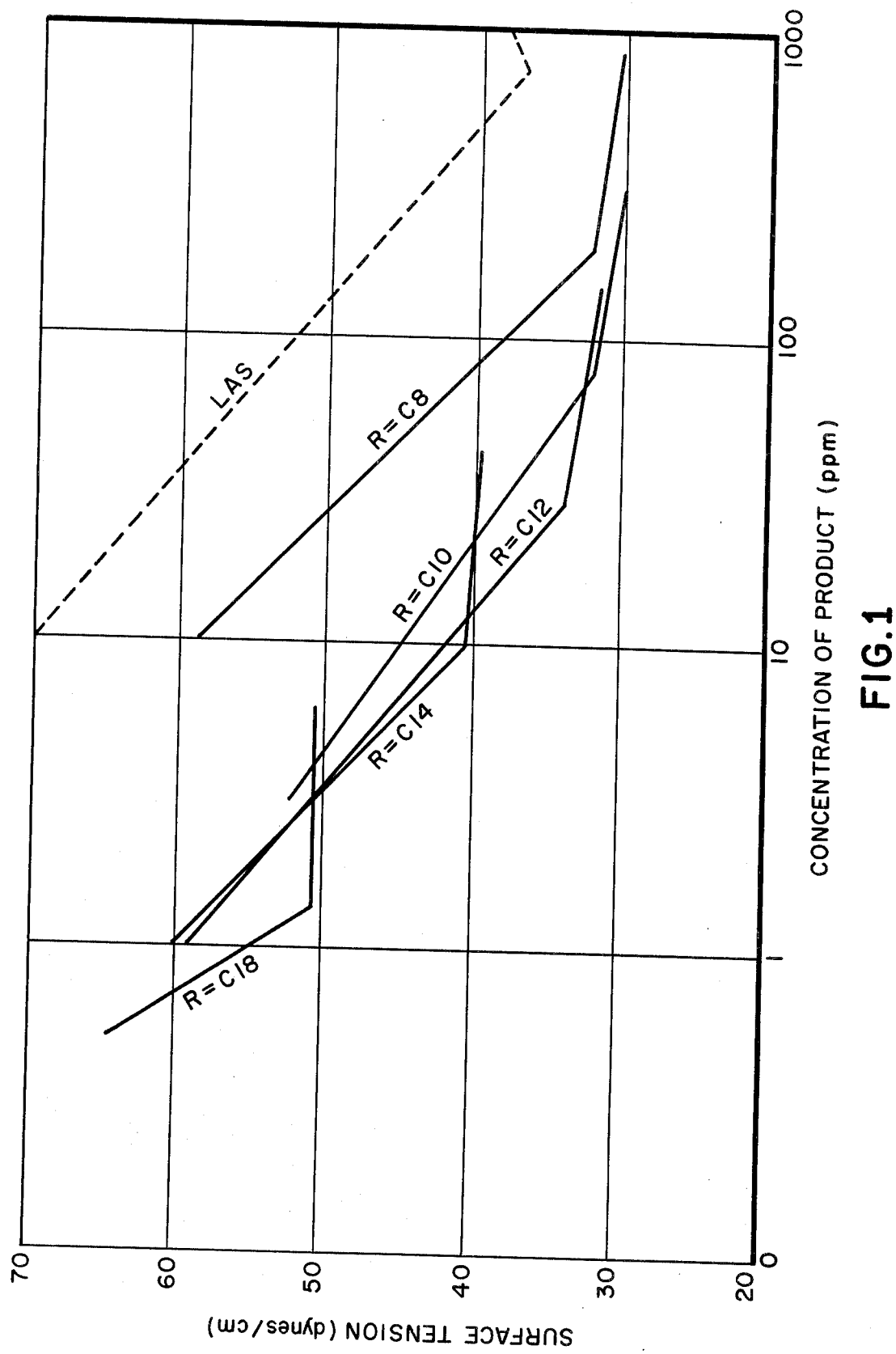

United States Patent

Gafa et al.

[11] 4,174,306
[45] Nov. 13, 1979

[54] DETERGENT COMPOSITIONS CONTAINING SELF-SEQUESTERING SURFACTANTS

[75] Inventors: Salvatore Gafa; Fulvio Burzio, both of Milan, Italy

[73] Assignee: Montedison S.p.A., Milan, Italy

[21] Appl. No.: 881,390

[22] Filed: Feb. 27, 1978

[30] Foreign Application Priority Data

Feb. 28, 1977 [IT] Italy .................... 20747 A/77

[51] Int. Cl.$^2$ .............................. C11D 1/04
[52] U.S. Cl. ...................... 252/546; 252/135; 252/89 R; 562/466; 562/470; 562/471; 562/583; 252/DIG. 11
[58] Field of Search .......... 252/89, 135, DIG. 11, 252/546; 260/520 P, 520 C, 521 P, 535 P, 501.15

[56] References Cited

U.S. PATENT DOCUMENTS

| | | | |
|---|---|---|---|
| 3,742,045 | 6/1973 | Lannert | 260/535 P |
| 3,784,486 | 1/1974 | Nelson et al. | 252/546 |
| 3,887,616 | 6/1975 | Lannert | 260/535 P |
| 3,970,698 | 7/1976 | Lannert | 260/535 P |
| 4,002,676 | 1/1977 | Borggrefe | 260/535 P |
| 4,017,541 | 4/1977 | Stubbs et al. | 260/535 P |

FOREIGN PATENT DOCUMENTS 2332539  1/1975  Fed. Rep. of Germany .

Primary Examiner—P. E. Willis, Jr.

[57] ABSTRACT

Detergent compositions containing self-requestering surfactants the molecules of which contain both a hydrophilic structure and a lipophilic structure are disclosed. The compositions comprise at least 5% by weight, of hydrosoluble salts having the formula

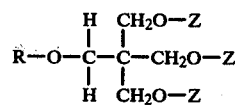

in which
R is alkyl, arylalkyl or alkylaryl of from 6 to 18 carbon atoms;
at least one of the groups represented by Z is a —$CH_2$—COO$^-$Me$^+$ carboxymethylene group in which Me$^+$ represents an ion selected from sodium, potassium and ammonium ions and from quaternary onium cations, and combinations thereof, and the remaining Z groups, which may be the same or different, represent H or a carboxymethylene as defined above.

9 Claims, 3 Drawing Figures

DETERGENT COMPOSITIONS CONTAINING SELF-SEQUESTERING SURFACTANTS

THE PRIOR ART

As is known, the detergent properties of conventional surfactants are considerably reduced when such surfactants are used in hard water, due to the presence of multivalent ions such as, for instance, calcium and magnesium cations, in the water. It is also known to avoid this disadvantage by adding, to the detergent compositions, a sequestering agent which will complex with the multivalent cations of the water and thus compensate for the harmful consequences of using the hard water.

Some of the known sequestering agents have a structure thanks to which they possess, besides the property of complexing with the multivalent cations, some appreciable additional (accessory) characteristics. Thus, some sequestering agents, commonly referred to as "builders", promote the stabilization of suspended solids, the emulsification of dirt particles, the activity of the surfactants, and the solubilization of water-insoluble materials. Moreover, such sequestering agents are compatible with other ingredients of the detergent compositions and are stable to hydrolysis when, as often happens, the compositions are used in hot alkaline baths. However, the major proportion of the "builders" known so far, for instance sodium tripolyphosphate and nitryl acetate, have the serious drawback of toxicity and in regard to environment protection, often causing eutrofication phenomena. The polluting effects of these sequestering compounds are discussed in detail in Italian Pat. No. 964,007.

Other inorganic sequestering agents based on alkaline carbonates and (poly)-silicates exhibit caustic and toxic effects that are too high for the sequestering agent to be used in the home, more particularly in dishwashers.

Another disadvantage of the known detergent compositions is that they require the separate synthesis of two different compounds: a surfactant and a "builder", which are then mixed in proportioned combinations.

THE PRESENT INVENTION

One object of this invention is to eliminate, or substantially reduce, the aforesaid drawbacks and disadvantages of the detergent compositions comprising the known sequestering agents.

Another object of the invention is to boost the detergent properties of detergent compositions containing a sequestering agent, under equal conditions, and without developing toxic and polluting properties.

These and other objects are accomplished by this invention which provides new detergent compositions which comprise at least one compound of the general formula

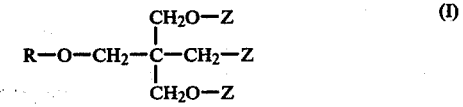

in which

R is alkyl, arylalkyl or alkylaryl having from 6 to 18 carbon atoms, and at least one of the three Z groups is a $-CH_2-COO^-Me^+$ carboxymethylene group in which $Me^+$ is selected from the group consisting of sodium, potassium and ammonium ions and quaternary onium cations, and combinations thereof, and the two remaining Z groups, which may be the same or different, represent either H or a $-CH_2-COO^-Me^+$ carboxymethylene group.

Examples of the useful quaternary onium cations are: tetramethylammonium, tetraethylammonium and the alkanol-ammonium ions. The formula (I) includes, also, mixed salts of sodium and potassium, sodium and ammonium, potassium and ammonium, etc., as well as mechanical mixes of different salts.

The compounds according to formula (I) are hydrosoluble salts and display the characteristics of self-sequestering surfactants. That is, besides surfactant properties, they possess autonomous sequestering capabilities (which is why they are termed "self-sequestering" herein) and do not require the help of a second, different and separate complexing compound. Said self-sequestering surfactants, henceforth referred to herein as TAS, eliminate problems of incompatibility between surfactants and sequestering agents, and simplify the mixing operations. They have, moreover, a low toxicity, a satisfactory biodegradability, do not irritate the skin and possess a low Krafft temperature.

These TAS compounds have, moreover, the important advantage that they can be mixed, as effective sequestering substances, with compositions already containing a conventional surfactant, for instance dodecylbenzenesulphonate or laurylsulphate, coupled with the additional advantage that, as compared with other known sequestering compounds and under equal conditions, they develop a greater detergent power without involving harmful environmental effects or exhibiting the other drawbacks and disadvantages of the known sequestering agents.

When the sequestering compounds of this invention are used in detergent compositions containing a different sequestering compound which has the drawbacks and disadvantages aforesaid, the concentration of that different sequestrant can be reduced, with a reduction in its toxic and polluting properties, provided a sequestrant TAS according to this invention is suitably integrated in such a detergent composition.

The self-sequestering compounds TAS form soluble complexes with calcium and magnesium cations sufficiently stable to eliminate the negative influence on the detergent properties of the compositions but which are not so stable as to cause an ecological imbalance (environmental disturbance) because of an accumulation of ions, as when sodium nitrylotriacetate is used. These environmental imbalances will appear even more remote when one considers that said TAS compounds form easily biodegradable complexes. They may be used safely in the washing of fabrics in general, including delicate fabrics, and for washing dishes. That is, the TAS compounds of this invention meet the requirements, as to formulation, and as expressed in English, for both HD (heavy duty) use and LD (light duty) use as well as meeting the formulation of detergents which are safe for use in the washing of dishes.

Another use of the TAS compounds of the invention consists in employing them as wetting agents in spinning, twisting, weaving and dyeing operations in the textile industry, especially in the presence of hard water.

The compositions according to this invention must contain at least 5%, but preferably between 5% and 60% by weight of hydrosoluble salts according to formula (I). The variation between 40% and 60% b.w. does not appreciably change the characteristics of the composition. When the basic constituent of a composition consists of a mixture of TAS and conventional surfactants and sequestering substances such as lauryl-sulphate, linear sodium dodecyl-benzene-sulphonate (henceforth referred to herein as LAS) and other anionic and non-ionic surfactants, sodium tripolyphosphate (henceforth) referred to herein as STPP), sodium pyrophosphate or potassium pyrophosphate, the percentage of conventional surfactant must be comprised between 0% and 40% b.w. with respect to the weight of the mixture of TAS and/or surfactant and/or sequestering agent, while the percentage of the conventional sequestering agent must range from 0 to 60% b.w. with respect to the weight of the mixture itself.

Said compositions may contain small quantities of the additives that are usually used in detergent compositions in order to make the composition more effective or more acceptable, for instance corrosion inhibitors, dyestuffs, perfumes, enzymes, anti-refouling agents, optical bleachers, fillers, foaming or anti-foaming agents and the like.

The TAS compounds according to the invention and the compositions that contain them take the different usual forms, for instance the form of powders, pearls, flakes, bars, soap cakes, paste, in liquid detergents and the like. The pH of the washing baths containing said compositions must be maintained between 7 and 12 but preferably between 9 and 11, by the addition of alkaline substances. The concentration of the composition in the bath may be comprised between 1 and 8 grams/liter.

As far as applicants are aware, TAS compounds according to the invention are new compounds and have been synthetized and tested for the first time by applicants. The best results have been obtained with salts in which the radical R consists of a linear alkyl chain containing from 10 to 14 carbon atoms.

There are various different methods for synthetizing the TAS compounds.

One method, exemplified infra, involves, firstly, the formation of an R—O—CH$_2$—C (CH$_2$OH)$_3$ ether-polyol starting from the correspondent alkyl halide RX and from pentaerythritol, HOCH$_2$—C(CH$_2$OH)$_3$.

Then the ether polyol is reacted with three moles of sodium chloroacetate. The two reactions may be conducted in electron-donor solvents, in the presence of alkalis.

The following examples are provided to describe the invention in more detail and are not intended to be limiting.

EXAMPLE 1 (Synthesis of TAS)

A mixture of 0.1 mole of pentaerythritol and 0.1 mole of NaOH was dissolved in anhydrous methanol and the solution was evaporated under vacuum. The dry residue was dispersed in 400 ml of dimethylsulphoxide in a flask fitted with a stirrer, a coolant and a drop funnel.

Thereupon, the dispersion was heated between 100° C. and 110° C. and into it were then introduced, under vigorous stirring, and over a period of 1 hour, 0.1 mole of alkyl halide dispersed in 100 ml of the same solvent. The temperature was maintained for about 3 hours until the pH attained neutrality, after which the solvent was evaporated under vacuum. The dry residue was repeatedly diluted under heat with chloroform or methylene chloride, and filtered each time.

The clear, filtered liquids were evaporated and the pure ether-polyol was isolated from the residue by crystallization from carbon tetrachloride. The purity of the product was determined on the basis of the steadiness of the melt point in successive crystallizations; the melt points are comprised between 35° and 76° C. for the different compounds of the series. The structure of the polyols was confirmed by the measurements under I.R. examination in comparison with products of similar structure previously synthetized and described in Italian Application 20513 A/76.

More particularly, for all the ether-polyols there were observed characteristic absorption bands in correspondence with the following wave lengths (in millimicron):

| | |
|---|---|
| 3100 | 7500 |
| 3500–3600 | 9000 |
| 6800 | 9500–9800 |
| 6900 | 11,200–11,300 |
| 7300 | 13,800 |

A mixture of 0.1 mole of ether-polyol and 0.3 mole of sodium hydrate was dissolved in anhydrous methanol and the solution was evaporated under vacuum. Thereupon the residue was dispersed in 500 ml of dimethylsulphoxide in a flask fitted with a stirrer, a reflux-condenser and a dropping funnel. This dispersion was heated to 100° C.–110° C., and 0.3 mole of sodium chloroacetate dispersed in 200 ccm of the same solvent was added under vigorous stirring and over a period of 1 hour, the temperature being maintained at 100° C.–110° C. for about 3 hours and until the pH of the mass was neutral, after which the mass was subjected to evaporation under vacuum.

Alternatively, the sodium salt of the reaction product was precipitated with acetone from the reaction mixture and then filtered and dried; the synthesis product was analyzed and it was found that it comprised about 50% b.w. of active substance.

The synthesis products were extracted, for analysis purposes, with ethyl ether in an acid form, from the corresponding aqueous solutions acidified with HCl and esterified with boron fluoride and methanol. More particularly, 300 mg. of active substance in an acid form were treated with 5 ml of a 14% solution of BF$_3$ in methanol, for a stretch of 10 minutes in a flask with a reflux cooler. Thereupon, the methyl ester was extracted with chloroform from the alcohol solution suitably diluted with water. A gas-chromatographic analysis proved that the products consisted prevailingly of the tricarboxylic derivative and of the bicarboxylic derivative, with small percentages of oxydiacetate of formula O(CH$_2$COONa)$_2$. In particular the following results were obtained; (the figures represent parts by weight):

| | R=C$_{10}$H$_{21}$ | R=C$_{12}$H$_{25}$ | R=C$_{14}$H$_{29}$ | R=C$_{18}$H$_{37}$ |
|---|---|---|---|---|
| oxydiacetate | 0.035 | 0.23* | 0.053 | 0.160 |
| dicarboxy-methylate | 0.730 | 0.98* | 0.190 | 0.190 |
| tricarboxy-methylate | 1. | 1. | 1. | 1. |

*These figures are presumed to be due to small changes during the preparation.

The theoretical degree of addition of the carboxymethylene groups to the polyols is equal to 3, but in practice the mean degree is comprised, as deduced from the foregoing tabulation, between 2.4 and 2.7. The sodium hydrate, by reacting with chloroacetate, gave place to the formation of sodium chloride. A potentiometric analysis with Ag/AgCl electrodes revealed an NaCl content almost corresponding to the theoretical or calculated content, thereby proving that chloroacetate had reacted completely, the chloroacetate fraction which did not take part in the carboxymethylation, being converted to oxydiacetate and other byproducts.

EXAMPLES 2-6 (ichthiotoxicity)

This series of examples concerns toxicity tests on fish of the Carassius Auratus species, for several TAS and for LAS. Table I indicates the concentrations in ppm of the compounds that cause a pre-fixed statistical mortality amongst fish.

TABLE I

| Ex. | Compound ($X = CH_2COONa, H$) | No mortality after 6 hours | Mortality of 50% of the cases after 6 hours |
|---|---|---|---|
| 2 | LAS | 7 ppm | 8.5 ppm |
| 3 | $C_8H_{17}$—O $CH_2$—$C(CH_2OX)_3$ | 150 ppm | >150 ppm |
| 4 | $C_{12}H_{25}$—O—$CH_2$—$C(CH_2OX)_3$ | 100 ppm | >100 ppm |
| 5 | $C_{16}H_{33}$—O—$CH_2$—$C(CH_2OX)_3$ | 70 ppm | 70-80 ppm |
| 6 | $C_{18}H_{37}$—O—$CH_2$—$C(CH_2OX)_3$ | 300 ppm | >300 ppm |

The toxicity of the TAS compounds is very low and at any rate extremely reduced with respect to the LAS compounds, which up to now, have been used in detergent compositions of largest consumption. The compounds of Examples 3, 4 and 6 do not cause any mortality or symptoms of intoxication even at concentrations greater than 100 ppm.

EXAMPLES 7-12 (sequestering power)

The sequestering power on calcium and magnesium ions represents one of the two basic functions of the TAS compounds of the invention and was evaluated by determining the constants of stability of the complexes formed by the calcium and by the magnesium with some of the compounds according to the invention. The results are recorded in Table II. The method used for the purpose consisted in potentiometric titrations with electrodes selective toward the ions in question, conducted under stationary conditions of ionic force ($10^{-2}$), pH and temperature (30° C.). During these titrations the quantity of ion complexed by a known quantity of kelating agent was measured, and the result of this measurement was used to calculate the constant of the complex. Example 7 (test with citrate) has been recorded in Table II for comparative purposes.

TABLE II

| Ex. | Kelating substance ($X = CH_2COONa, H$) | $K_{Ca^{++}}$ pH = 10.5 | $K_{Mg^{++}}$ pH = 9.5 |
|---|---|---|---|
| 7 | Sodium citrate | $1.03 \cdot 10^4$ | $1.04 \cdot 10^4$ |
| 8 | $C_{10}H_{21}$—O—$CH_2$—$C(CH_2OX)_3$ | $0.86 \cdot 10^4$ | $0.32 \cdot 10^4$ |
| 9 | $C_{12}H_{25}$—O—$CH_2$—$C(CH_2OX)_3$ | $0.98 \cdot 10^4$ | $0.46 \cdot 10^4$ |
| 10 | $C_{14}H_{29}$—O—$CH_2$—$C(CH_2OX)_3$ | $0.9 \cdot 10^4$ | $0.42 \cdot 10^4$ |
| 11 | $C_{16}H_{33}$—O—$CH_2$—$C(CH_2OX)_3$ | $0.4 \cdot 10^4$ | $0.2 \cdot 10^4$ |
| 12 | $C_{18}H_{37}$—O—$CH_2$—$C(CH_2OX)_3$ | $2.1 \cdot 10^4$ | $0.81 \cdot 10^4$ |

The TAS compounds of the invention develop a good complexing power toward calcium and magnesium cations, altogether comparable with citrate, considered a good sequestering agent, and with possibilities of substitution, on the industrial scale, of tripolyphosphate.

Figure 2:
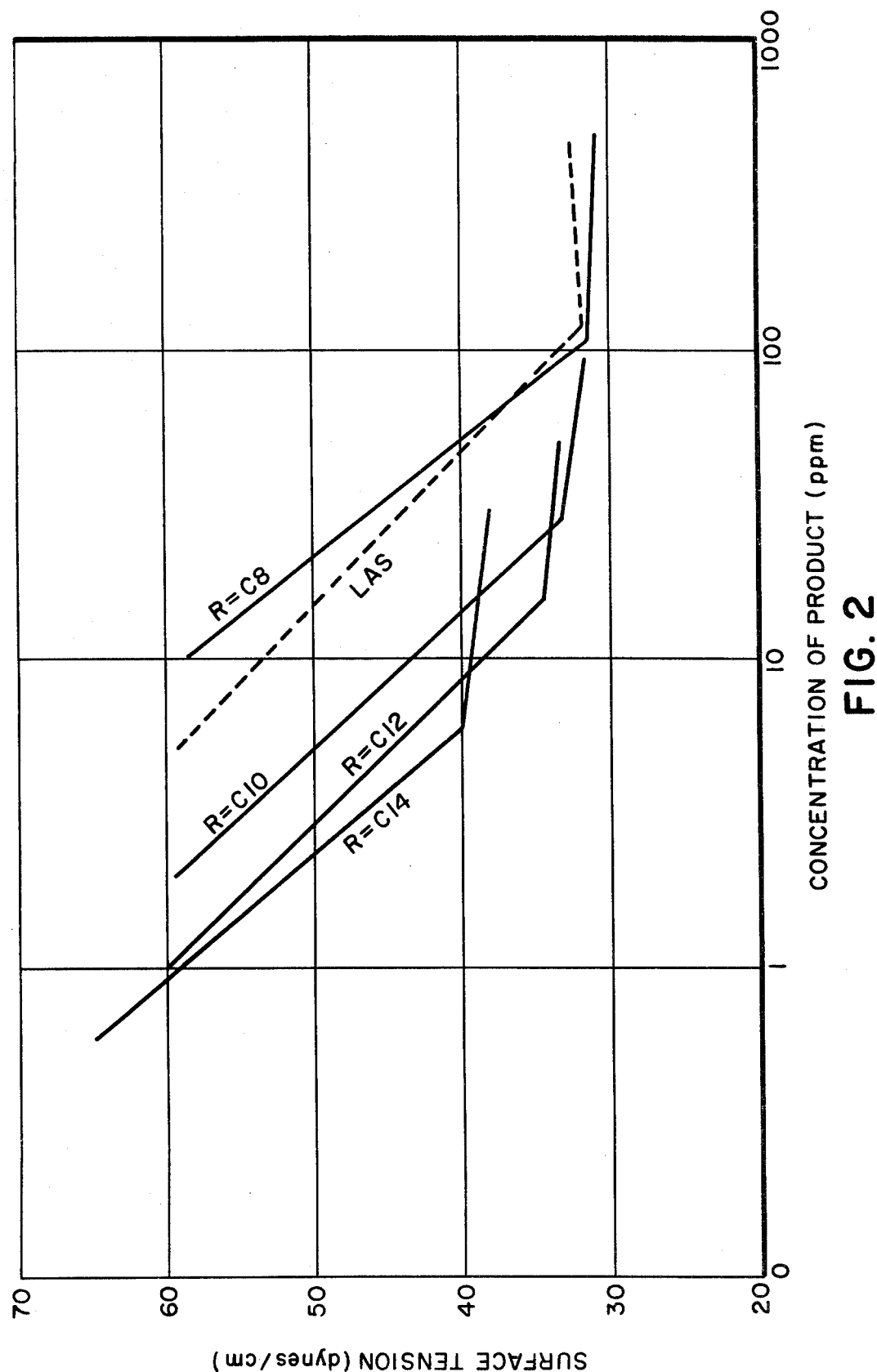
Figure 3:
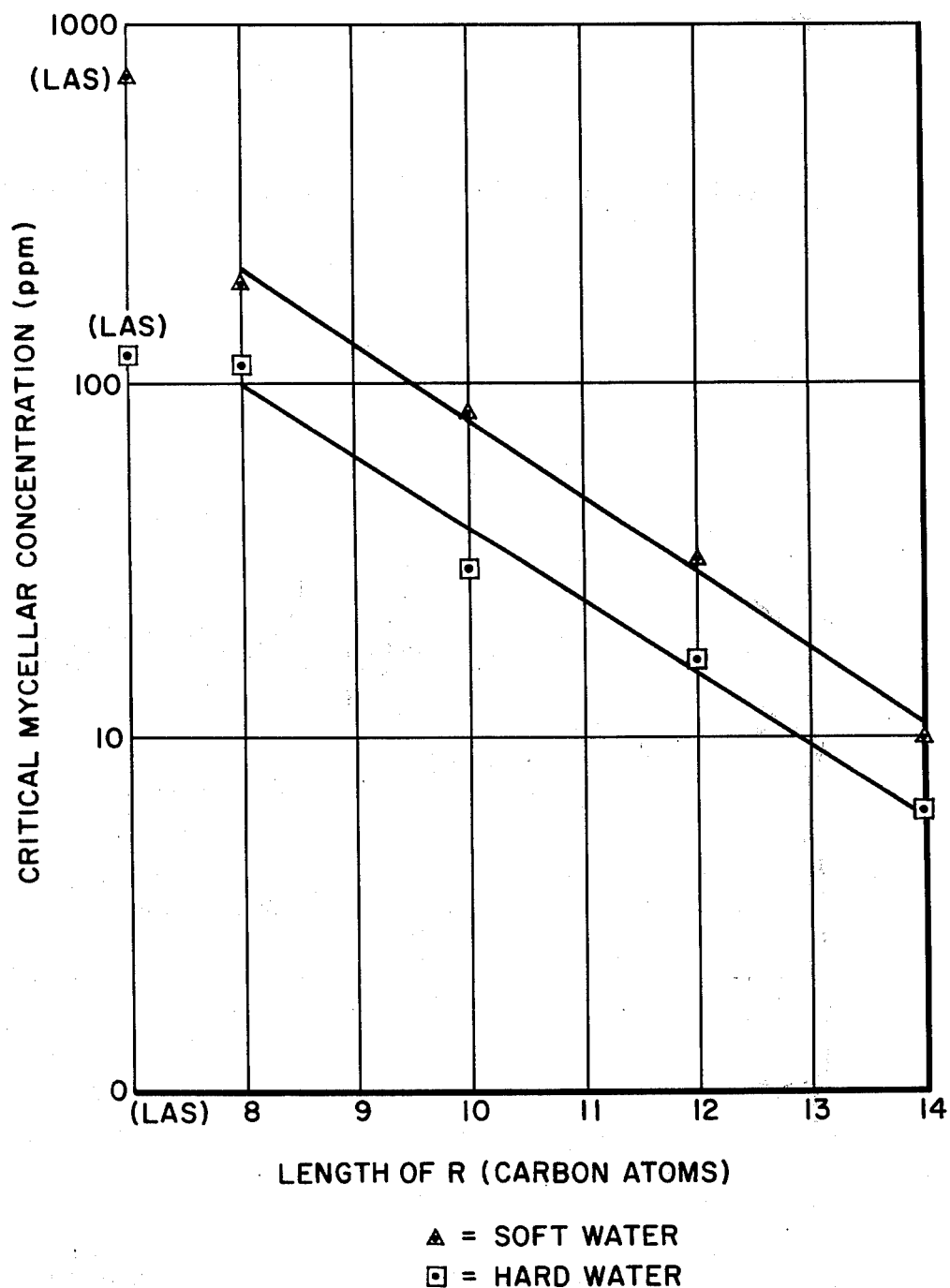

In the accompanying drawings:

FIG. 1 is a graph showing the results of testing the effect, at equal concentrations, of known LAS compounds and of TAS compounds according to this invention on the surface tension of soft water as described in Examples 13-19;

FIG. 2 is a graph showing the results of testing the effect, at equal concentrations, of known LAS compounds and of TAS compounds according to this invention on the surface tension of hard water as described in Examples 20-26; and FIG. 3 is a graph showing that the effectiveness of known LAS compounds and of TAS compounds according to the invention, as simultaneous surfactants and "builders" in soft and hard water is less influenced by the critical micellar concentration (cmc) than by the number of carbon atoms in radical R.

EXAMPLES 13-19 (Surface Tension In Soft Water)

There were prepared solutions of different concentrations in distilled water, of LAS compounds and of the sodium salts of formula R—O—$CH_2$—$C(CH_2OZ)_3$ in which R represents a linear alkyl radical containing respectively 8, 10, 12, 14 and 18 carbon atoms and Z is $CH_2COONa,H$. The samples of the solutions were maintained at a temperature of 20° C. for 24 hours, after which they were subjected to tensiometric tests with a semi-automatic Fisher Surface Tensiomat ring-tensiometer.

The results of the tests are represented diagrammatically in the graph of FIG. 1 of the accompanying drawings, and it will be noted that the TAS compounds according to this invention are more effective, at equal concentration, that the LAS compounds in reducing the surface tension of the water, in the absence of sources of hardness.

EXAMPLES 20-26 (Surface Tension In Hard Water)

Solutions of different concentrations of known LAS compounds and of TAS compounds according to the invention were prepared according to Examples 13-19, in water containing calcium and magnesium salts according to a molar ratio $Ca^{++}$: $Mg^{++}$=2:1. Said water had a hardness degree of 10 French degrees and contained the following salts: $Na_2SO_4$ 39.6 mg/lt; NaCl 14.4 mg/lt; $NaNO_3$ 4.4 mg/lt; $NaHCO_3$ 136 mg/lt.

The same water was used for the ichthio-toxicity tests. The surface tension tests were carried out according to Examples 13-19, the results being shown in the graph of FIG. 2 of the drawings. The tests in hard water lead to a lowering of the surface tension in a much higher degree than the tests carried out in soft water (at equal concentration of surfactant) and this phenomenon is more evident for the LAS compound than for the TAS compounds. When the surface tensions of the aqueous solutions of the surfactants are transferred to a semi-logarithmic diagram as a function of the concentrations (see FIGS. 1 and 2), the curves obtained are broken into two by a discontinuity point in correspondence with a concentration that is defined as critical micellar concentration (in abbreviated form cmc).

When the water of the solutions is hard, the effect of the anionic compounds on the surface tension is increased and the cmc is reduced. As can be seen from FIGS. 1 and 2, when passing from soft water to hard water the cmc of the known LAS compounds suffers a consistent drop, while the reduction of the cmc of the TAS compounds is definitely less marked.

As a matter of fact, it may be said that the cmc of the TAS compounds, as an expression of their function as simultaneous surfactants and builders, is less influenced by the hardness of the water as compared to the common anionic surfactants. This concept is better understood from consideration of FIG. 3 of the drawings, where the critical micellar concentrations in soft and in hard water for the LAS and TAS compounds are traced as a function of the number of carbon atoms in radical R.

EXAMPLES 27-32 (Foaming Power)

Two sets of tests were carried out. The first was carried out on an Emmendi Dubbini test apparatus. The method consists in determining how many cubic centimeters of foam are formed by mechanical stirring at 20° C., of 300 ml of an aqueous solution containing one gram of the product being tested, per liter.

The second method is the so-called Ross-Miles method and consists in measuring how many cubic centimeters (cc) of foam are formed when 500 ml of the above indicated solution are allowed to fall through a calibrated or gauged pipe from a constant height and at a constant temperature (20° C.), into a vessel containing 50 ml of the same solution.

The results of the tests recorded in Table III show that the TAS compounds of this invention have a foaming behavior which is altogether similar to that of the known LAS compounds.

TABLE III

| | | VOLUME OF FOAM (cubic centimeters) | | | | | |
|---|---|---|---|---|---|---|---|
| | | Emmedi Dubbini | | | | | |
| | | After | After 100 blows | | | | |
| | Compound | 50 | | t = 5' | Ross-Miles | | |
| Ex. | (X = $CH_2COONa$, H) | blows | initial | (x) | initial | t = 1' | t = 3' | t = 5' |
| 27 | LAS | 540 | 565 | 560 | 360 | 350 | 350 | 350 |
| 28 | $C_8H_{17}$—O—$CH_2$—$C(CH_2OX)_3$ | 545 | 570 | 560 | 290 | 270 | 260 | 250 |
| 29 | $C_{10}H_{21}$—O—($CH_2$—$C(CH_2OX)_3$ | 555 | 610 | 600 | 300 | 290 | 280 | 280 |
| 30 | $C_{12}H_{25}$—O—$CH_2$—$C(CH_2OX)_3$ | 545 | 580 | 570 | 320 | 290 | 290 | 290 |
| 31 | $C_{14}H_{29}$—O—$CH_2$—$C(CH_2OX)_3$ | 510 | 570 | 560 | 280 | 270 | 260 | 260 |
| 32 | $C_{18}H_{37}$—O—$CH_2$—$C(CH_2OX)_3$ | 485 | 515 | 510 | 200 | 190 | 185 | 180 |

(x) t = rest time in minutes between stoppage of mechanical action or dropping of the solution and the moment of the measuring.

EXAMPLES 33-53 (Heavy-duty Detergency)

A series of detergent tests was carried out in hard water (20 French degrees, molar ratio $Ca^{++}/Mg^{++}=2:1$) on different cotton fabrics. The tests were carried out at 60° C. in a Terg-O-Tometer apparatus built by U.S. Testing Company on test pieces (specimen) of fabric soiled artifically in a standard way, washed for 20 minutes under stirring at 100 cycl./min. in a washing bath containing 4 g/lt. of detergent formulation of the following composition (heavy-duty):

- basic mixture (see Tables IV, V and VI)—60% by weight
- $2SiO_2.Na_2O$—8% by weight
- Carboxymethylcellulose (CMC)—1% by weight
- Sodium sulphate+sodium chloride—to bring to 100%.

The degree of detergency was determined by evaluating the mean increments (increases) of reflectance ($\Delta R$) of the washed test-pieces, rinsed and dried in the air in comparison with the original soiled test-pieces. The reflectance was determined by means of an Elrepho Zeiss electrophotometer, operating with a No. 6 screen, assuming the reflectance of pure magnesium oxide equal to 100 and the reflectance of the black body equal to zero.

The detergency tests on cotton fabrics were carried out on the following types:
- EMPA 101 cotton (St. Gallen—CH)
- Cotton of Testfabrics, Inc. (Middlesex, N.J., USA)
- Cotton of the U.S. Testing Company (USA)

and the results of said tests are reported in Tables IV, V, and VI, respectively, in comparison with blank tests carried out in water only.

TABLE IV

| Ex. | Basic mixture = LAS and/or STPP and/or TAS (X = $CH_2COONa$,H) | % by weight (x) | $\Delta R$ |
|---|---|---|---|
| 33 | Blank test | — | 5.7 |
| 34 | LAS | 25 | |
| | + STPP | 35 | 29.6 |
| 35 | $C_8H_{17}$—O—$CH_2$—$C(CH_2OX)_3$ | 60 | 15.4 |
| 36 | $C_{10}H_{21}$—O—$CH_2$—$C(CH_2OX)_3$ | 60 | 25.7 |
| 37 | $C_{12}H_{25}$—O—$CH_2$—$C(CH_2OX)_3$ | 60 | 27.4 |
| 38 | $C_{18}H_{37}$—O—$CH_2$—$C(CH_2OX)_3$ | 60 | 29.2 |
| 39 | $C_8H_{17}$—O—$CH_2$—$C(CH_2OX)_3$ | 35 | |
| | + LAS | 10 | |
| | + STPP | 15 | 26.6 |
| 40 | $C_{10}H_{21}$—O—$CH_2$—$C(CH_2OX)_3$ | 35 | |
| | + LAS | 10 | |
| | + STPP | 15 | 28. |
| 41 | $C_{12}H_{25}$—O—$CH_2$—$C(CH_2OX)_3$ | 35 | |
| | + LAS | 10 | |
| | + STPP | 15 | 28.3 |
| 42 | $C_{14}H_{29}$—O—$CH_2$—$C(CH_2OX)_3$ | 35 | |
| | + LAS | 10 | |
| | + STPP | 15 | 26.9 |
| 43 | $C_{18}H_{37}$—O—$CH_2$—$C(CH_2OX)_3$ | 35 | |
| | + LAS | 10 | |
| | + STPP | 15 | 28.6 |

(x) based on the total weight of the composition.

TABLE V

| | TESTFABRICS INC. - Cotton | | |
|---|---|---|---|
| Ex. | Basic mixture = LAS and/or STPP and/or TAS (X = $CH_2COONa$, H) | % by weight (x) | $\Delta R$ |
| 44 | Blank test | — | 5.8 |
| 45 | LAS | 25 | |
| | + STPP | 35 | 14.4 |
| 46 | $C_{10}H_{21}$—O—$CH_2$—$C(CH_2OX)_3$ | 60 | 12.3 |
| 47 | $C_{12}H_{25}$—O—$CH_2$—$C(CH_2OX)_3$ | 60 | 14.3 |
| 48 | $C_{18}H_{37}$—O—$CH_2$—$C(CH_2OX)_3$ | 60 | 13.9 |

(x) based on the total weight of the composition.

TABLE VI

U.S. TESTING Co. - Cotton

| Ex. | Basic mixture = LAS and/or STPP and/or TAS (X = CH$_2$COONa, H) | % by weight (x) | ΔR |
|---|---|---|---|
| 49 | Blank test | — | 1.4 |
| 50 | LAS | 25 | |
|  | + STPP | 35 | 5.0 |
| 51 | C$_{10}$H$_{21}$—O—CH$_2$—C(CH$_2$OX)$_3$ | 60 | 4.8 |
| 52 | C$_{12}$H$_{25}$—O—CH$_2$—C(CH$_2$OX)$_3$ | 60 | 5.6 |
| 53 | C$_{18}$H$_{37}$—O—CH$_2$—C(CH$_2$OX)$_3$ | 60 | 5.7 |

(x) based on the total weight of the composition.

EXAMPLES 54–67 (Heavy-duty Detergency)

On three cotton fabrics of the Examples 33–53 there were carried out under the same conditions, detergency tests conforming to American commercial formulations free from phosphates such as TIDE (Procter & Gamble) and WISK (Lever) having the following compositions:

TIDE (powder):
LAS—12%
Na-alkyl-ethoxysulphate—9%
Sodium carbonate—20%
Sodium silicate—20%
Sodium sulphate—29%
Carboxymethyl cellulose and H$_2$O—10%

WISK (liquid):
LAS—12%
Ethoxylated alcohol—11%
Hydrotropes—8%
Sodium sulphate—1.5%
Carboxymethyl cellulose and other additives—11%
Water—57.5%

The comparison was carried out with formulations containing TAS compounds of this invention and having the following composition:
TAS—30%
2SiO$_2$.Na$_2$O—8%
Carboxymethyl cellulose—1%
Na$_2$SO$_4$+NaCl—31%
H$_2$O—up to 100%

The mean reflectance increments for the three cotton fabrics were determined and are recorded in Tables VII, VIII and IX.

TABLE VII

EMPA 101 - Cotton

| Ex. No. | TAS or commercial formulate (X = CH$_2$COONa, H) | ΔR |
|---|---|---|
| 54 | TIDE | 28.7 |
| 55 | WISK | 11.2 |
| 56 | C$_{10}$H$_{21}$—O—CH$_2$—C(CH$_2$OX)$_3$ | 18.8 |
| 57 | C$_{12}$H$_{25}$—O—CH$_2$—C(CH$_2$OX)$_3$ | 23.5 |
| 58 | C$_{14}$H$_{29}$—O—CH$_2$—C(CH$_2$OX)$_3$ | 20.0 |
| 59 | C$_{18}$H$_{37}$—O—CH$_2$—C(CH$_2$OX)$_3$ | 18.7 |

TABLE VIII

TESTFABRICS INC. - Cotton

| Ex. No. | TAS or commercial formulate (H = CH$_2$COONa, H) | ΔR |
|---|---|---|
| 60 | TIDE | 18.8 |
| 61 | WISK | 13.8 |
| 62 | C$_{12}$H$_{25}$—O—CH$_2$—C(CH$_2$OX)$_3$ | 13.9 |
| 63 | C$_{18}$H$_{37}$—O—CH$_2$—C(CH$_2$OX)$_3$ | 11.5 |

TABLE IX

U.S. TESTING CO. - Cotton

| Ex. No. | TAS or commercial formulate (X = CH$_2$COONa, H) | ΔR |
|---|---|---|
| 64 | TIDE | 7.3 |
| 65 | WISK | 7.4 |
| 66 | C$_{12}$H$_{25}$—O—CH$_2$—C(CH$_2$OX)$_3$ | 5.7 |
| 67 | C$_{18}$H$_{37}$—O—CH$_2$—C(CH$_2$OX)$_3$ | 3.8 |

EXAMPLES 68–82 (Light-duty Detergency)

A series of detergency tests were carried out on various wool fabrics in hard water (20 French degrees, and at a molar ratio Ca$^{++}$/Mg$^{++}$=2:1). These tests were conducted at 40° C. on a Terg-O-Tometer on test-pieces of fabrics artificially soiled in a standard way, washed for 20 minutes with a 75 cycl./min. stirring in a washing bath containing 4 g/lt. of detergent formulate. For comparative purposes a number of commercial formulates for delicate fabrics, and having the following compositions, were evaluated:

|  | % by Weight |
|---|---|
| IVORY liquid (Procter & Gamble - USA) | |
| Diethanolamide | 7. |
| Alkylethoxyammonium sulphate | 31.5 |
| Water | 61.5 |
| LUX liquid (Lever - USA) | |
| LAS | 16. |
| Alkylethoxyammonium sulphate | 9.5 |
| Diethanolamide | 7. |
| Hydrotropes | 9. |
| Water | 58.5 |
| LIP Cashmire liquid (Mira Lanza - Italy) | |
| LAS | 17. |
| Alkylethoxysulphate | 6. |
| Amide | 3. |
| Hydrotropes | 7. |
| Water | 67. |

The composition of the formulate containing TAS is the following:
TAS—40% by weight
Water—60% by weight The mean reflectance increments (ΔR) were determined as in Examples 33–53 (see Tables V, VI and VIII). The detergency tests were carried out on the following wool fabrics:
Empa 102 wool,
Testfabrics wool,
U.S. Testing Company wool, and the results were recorded, respectively, in Tables X, XI and XII, and compared with blank tests carried out in water only.

TABLE X

EMPA 102 - Wool

| Ex. No. | TAS or commercial formulate (X = CH$_2$XOONa, H) | ΔR |
|---|---|---|
| 68 | Blank test | 0 |

TABLE X-continued

EMPA 102 - Wool

| Ex. No. | TAS or commercial formulate (X = CH$_2$XOONa, H) | ΔR |
|---|---|---|
| 69 | IVORY | 14.2 |
| 70 | LUX | 15.6 |
| 71 | LIP | 14.3 |
| 72 | C$_{12}$H$_{25}$—O—CH$_2$—C(CH$_2$OX)$_3$ | 15.1 |

TABLE XI

TESTFABRICS INC. - Wool

| Ex. No. | TAS or commercial formulate (X = CH$_2$COONa, H) | ΔR |
|---|---|---|
| 73 | Blank test | 0.4 |
| 74 | IVORY | 31.1 |
| 75 | LUX | 12.3 |
| 76 | LIP | 22.8 |
| 77 | C$_{12}$H$_{25}$—O—CH$_2$—C(CH$_2$OX)$_3$ | 16.4 |

TABLE XII

U.S. TESTING CO. - Wool

| Ex. No. | TAS or commercial formulate (X = CH$_2$COONa, H) | ΔR |
|---|---|---|
| 78 | Blank test | 0. |
| 79 | IVORY | 7.6 |
| 80 | LUX | 8.2 |
| 81 | LIP | 8.1 |
| 82 | C$_{12}$H$_{25}$—O—CH$_2$—C(CH$_2$OX)$_3$ | 6.3 |

EXAMPLES 83-85 (Biodegradability)

Biodegradability tests were carried out on some TAS by means of BOD tests (Biochemical Oxygen Demand) and of COD tests (Chemical Oxygen Demand). The results obtained are recorded in Table XIII. The COD values represent the amount of oxygen in milligrams necessary for a complete combustion to water and carbon dioxide; the figures are referred to 500 mg of TAS and are directly comparable with the BOD values (the experimental COD value was obtained by oxidizing with potassium dichromate). The BOD values express the amount of oxygen in milligrams absorbed by one liter of aqueous solution containing 500 mg of TAS subjected to the biodegradability tests according to W. K. Fischer (Tenside: volume 8, No. 4; 1971, page 182) with only partially acclimatized inoculation, after, 5, 15 and 30 days of treatment. According to this method, a substance may be considered as biodegradable when the BOD on the 30th day is higher than 40% of the experimental COD.

TABLE XIII

| Ex. No. | Surfactant (X = CH$_2$COONa, H) | Exp. COD | BOD 5 days | BOD 15 days | BOD 30 days | BOD:COD 30 days (%) |
|---|---|---|---|---|---|---|
| 83 | C$_{10}$H$_{21}$—O—C(CH$_2$OX)$_3$ | 192 | 19 | 71.5 | 76 | 40 |
| 84 | C$_{12}$H$_{25}$—O—C(CH$_2$OX)$_3$ | 204 | 26 | 51.5 | 63 | 35 |
| 85 | C$_{14}$H$_{29}$—O—C(CH$_2$OX)$_3$ | 180 | 32 | 86.5 | 93 | 52 |

What is claimed is:

1. Self-sequestering surfactants having the following general formula (I):

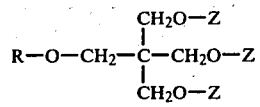

in which
R is alkyl, arylalkyl or alkylaryl containing from 6 to 18 carbon atoms; and
at least two Z groups are a CH$_2$—COO$^-$Me$^+$ carboxymethylene group in which me$^+$ is an ion selected from the group consisting of sodium, potassium and ammonium ions or a quarternary onium cation, or combinations of the same and any Z group which is not a CH$_2$—COO$^-$Me$^+$ carboxymethylene group as defined is a hydrogen atom.

2. Detergent compositions containing, as the essential constituent thereof, at least 5% by weight of at least one self-sequestering surfactant according to claim 1.

3. Detergent compositions containing, as the essential constituent thereof, at least 5% by weight of at least one self-sequestering surfactant according to claim 1, and in which R of formula (I) is a linear chain containing from 12 to 14 carbon atoms.

4. Detergent compositions containing, as the essential constituent thereof, from 5% to 60% by weight of at least one self-sequestering surfactant according to claim 1.

5. The method of washing water-washable articles which consists in washing the articles in water containing a detergent composition according to claim 2.

6. The method of claim 5, in which the articles washed are fibrous materials.

7. The method of claim 5, in which the articles washed are articles used in the preparation and serving of food.

8. The method of preparing fibers for spinning, twisting, weaving, felting and dyeing operations which comprises wetting the fibers with a detergent composition according to claim 1.

9. Self-sequestering surfactants having the following general formula (I):

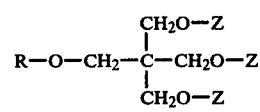

in which
R is alkyl, arylalkyl or alkylaryl containing from 6 to 18 carbon atoms; and
at least two Z groups are CH$_2$—COO$^-$Me$^+$ carboxymethylene groups in which Me$^+$ is an ion selected from the group consisting of sodium, potassium and ammonium ions or a univalent cation, or combinations of the same and any Z group which is not a CH$_2$COO$^-$Me$^+$ carboxymethylene group as defined is a hydrogen atom.

* * * * *